(12) United States Patent
Onodera et al.

(10) Patent No.: US 10,018,587 B2
(45) Date of Patent: Jul. 10, 2018

(54) METHOD FOR DETERMINING WHETHER A CAPILLARY FILLED WITH AN ELECTROPHORESIS MEDIUM CAN BE USED SUITABLY FOR ELECTROPHORESIS

(71) Applicant: Panasonic Intellectual Property Management Co., Ltd., Osaka (JP)

(72) Inventors: Mari Onodera, Osaka (JP); Hidenobu Yaku, Hyogo (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 41 days.

(21) Appl. No.: 15/279,548

(22) Filed: Sep. 29, 2016

(65) Prior Publication Data

US 2017/0315087 A1    Nov. 2, 2017

(30) Foreign Application Priority Data

Apr. 27, 2016 (JP) ................................. 2016-088779

(51) Int. Cl.
| | |
|---|---|
| *G01N 27/416* | (2006.01) |
| *G01N 27/447* | (2006.01) |
| *G01N 27/06* | (2006.01) |

(52) U.S. Cl.
CPC ......... *G01N 27/4163* (2013.01); *G01N 27/06* (2013.01); *G01N 27/44791* (2013.01)

(58) Field of Classification Search
CPC ................................................ G01N 27/4163
See application file for complete search history.

(56) References Cited

U.S. PATENT DOCUMENTS

| | | | | |
|---|---|---|---|---|
| 5,358,613 A | * | 10/1994 | Schneider | ........ G01N 27/44743 204/453 |
| 2002/0151039 A1 | * | 10/2002 | Wittwer | .................... B01L 7/52 435/286.1 |

FOREIGN PATENT DOCUMENTS

| | | |
|---|---|---|
| JP | 61-080450 U | 5/1986 |
| JP | 2-234060 | 9/1990 |
| JP | 2-269953 | 11/1990 |
| JP | 7-239313 | 9/1995 |
| JP | 11-142355 | 5/1999 |
| JP | 2004-333190 | 11/2004 |
| JP | 2009-156604 | 7/2009 |
| JP | 2009-250706 | 10/2009 |

* cited by examiner

*Primary Examiner* — Clayton E Laballe
*Assistant Examiner* — Jas Sanghera
(74) *Attorney, Agent, or Firm* — McDermott Will & Emery LLP

(57) ABSTRACT

The present invention provides a method for determining whether or not a capillary filled with an electrophoretic medium is suitably used for electrophoresis before electrophoresis is performed using the analytes. The method comprises (a) applying an alternating-current voltage between a first electrode which is in contact with a first electrolyte solution in which one end of the capillary is immersed and a second electrode which is in contact with a second electrolyte solution in which the other end of the capillary is immersed to measure an electric conductivity of the electrophoresis medium with which an inside of the capillary is filled; and (b) determining that the capillary filled with the electrophoresis medium fails to be used suitably for the electrophoresis, when the electric conductivity is more than 4.2 mS/cm.

6 Claims, 13 Drawing Sheets

METHOD FOR DETERMINING WHETHER A CAPILLARY FILLED WITH AN ELECTROPHORESIS MEDIUM CAN BE USED SUITABLY FOR ELECTROPHORESIS

BACKGROUND

1. Technical Field

The present invention relates to a method for determining whether or not a capillary filled with an electrophoresis medium can be used suitably for electrophoresis.

2. Description of the Related Art

In a capillary electrophoresis method, first, analytes are supplied into a capillary filled with an electrophoretic medium such as a buffer solution. Then, a high voltage is applied to the electrophoretic medium and the analytes to separate the analytes from one another due to difference of electric charges of the analytes.

Japanese Patent Application laid-open Publication No. Hei 2-269953 discloses a capillary electrophoresis device. In this device, analytes are supplied into a capillary filled with an electrophoretic medium such as a buffer solution, while pressure is applied to the analytes. Then, a direct-current voltage is applied to the both ends of the capillary. The operation of the capillary electrophoresis device is controlled by a sequencer.

Repeats of trials and errors are required to determine whether or not a capillary filled with an electrophoretic medium can be used suitably for electrophoresis in a conventional capillary electrophoresis device. When a capillary is filled with an inappropriate electrophoretic medium, an abnormal baseline occurs. The abnormal baseline is not flat. For example, the abnormal baseline has a protrusion and a recess. For this reason, a peak derived from the analytes failed to be detected.

It is difficult to determine whether or not a capillary is filled suitably with an electrophoretic medium before electrophoresis is performed using the analytes. Therefore, in a case where a capillary is filled with an inappropriate electrophoretic medium, the analytes are wasted.

SUMMARY

The present invention provides a method for determining whether or not a capillary filled with an electrophoresis medium can be used suitably for electrophoresis, the method comprising;

(a) applying an alternating-current voltage between a first electrode which is in contact with a first electrolyte solution in which one end of the capillary is immersed and a second electrode which is in contact with a second electrolyte solution in which the other end of the capillary is immersed to measure an electric conductivity of the electrophoresis medium with which an inside of the capillary is filled; and (b) determining that the capillary filled with the electrophoresis medium fails to be used suitably for the electrophoresis, when the electric conductivity is more than 4.2 mS/cm.

The present invention provides a method for determining whether or not a capillary filled with an electrophoretic medium is suitably used for electrophoresis before electrophoresis is performed using analytes.

DETAILED DESCRIPTION OF THE EMBODIMENT

The embodiment of the present invention will be described with reference to the drawings.

(Capillary Electrophoresis Device)

Figure 1:
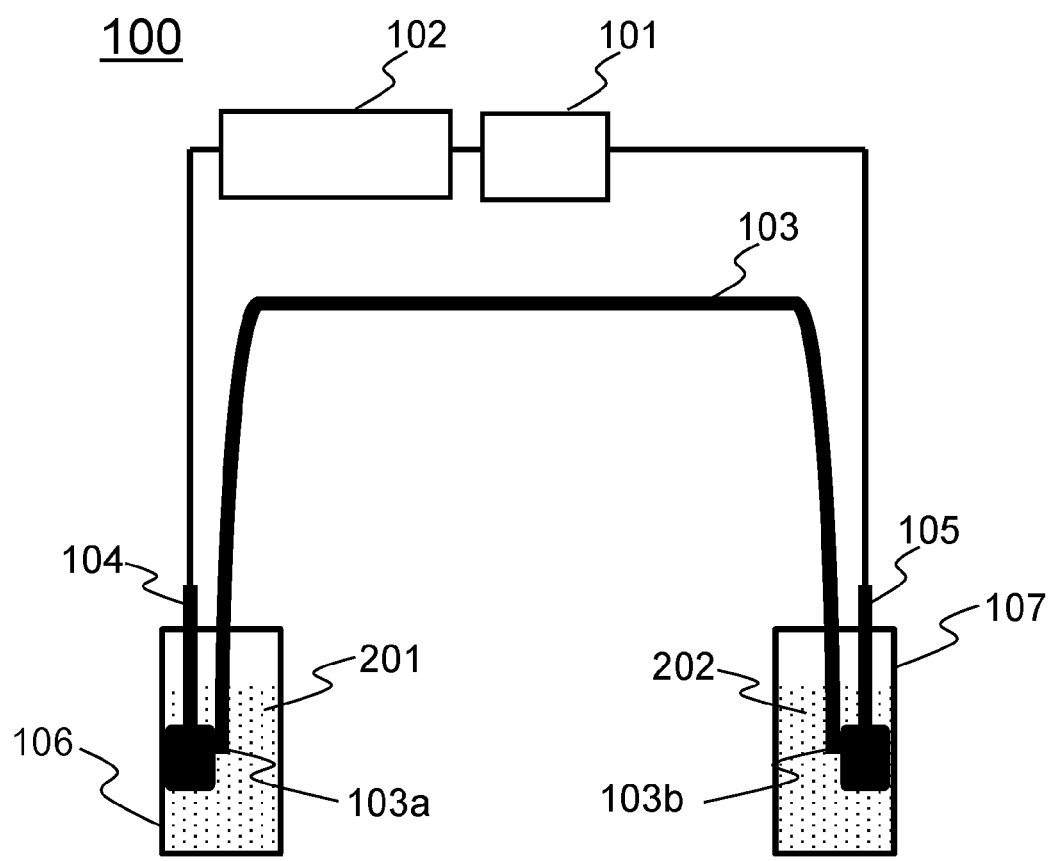
FIG. 1 shows a schematic view of a capillary electrophoresis device 100 according to the embodiment.

FIG. 1 shows a schematic view of a capillary electrophoresis device 100 according to the embodiment. The capillary electrophoresis device 100 comprises a power supply 101, a control unit 102, a capillary 103, a first electrode 104, a second electrode 105, a first container 106, and a second container 107.

(First Container 106 and First Electrode 104)

The first container 106 contains a first electrolyte 201. One end 103a of the capillary 103 is immersed in the first electrolyte 201. The first container 106 comprises the first electrode 104. The first electrode 104 is in contact with the first electrolyte 201. The first electrode 104 is electrically connected to the power supply 101. An example of the material of the first electrode 104 is titanium, chrome, tungsten, copper, aluminum, platinum, or an alloy thereof. It is desirable that the first electrode 104 has a shape of a flat plate. The material of the first container 106 is not limited, as long as the first container does not react with an electrophoretic medium and the first electrolytes 201. An example of the material of the first container 106 is glass or resin (e.g., polystyrene or polymethylmethacrylate).

(Second Container 107 and Second Electrode 107)

Similarly, the second container 107 contains a second electrolyte 202. The other end 103b of the capillary 103 is immersed in the second electrolyte 202. The second container 107 comprises the second electrode 105. The second electrode 105 is in contact with the second electrolyte 202. The second electrode 105 is electrically connected to the power supply 101. Examples of the material and the shape of the second electrode 105 are similar to those of the first electrode 104. An example of the material of the second container 107 is also similar to that of the first container 106.

(Power Supply 101)

The power supply 101 is located electrically between the first electrode 104 and the second electrode 105. Using the power supply 101, an alternating-current voltage or a direct-current voltage is applied between the first electrode 104 and the second electrode 105. The alternating-current voltage may have a frequency of not less than 200 hertz and not more than 3,000 hertz and a voltage of not less than 2,000 volts and not more than 30,000 volts. The direct-current voltage may have a voltage of not less than 2,000 volts and not more than 30,000 volts.

(Capillary 103)

The capillary 103 is filled with an electrophoretic medium. It is desirable that the material of the electrophoretic medium is the same as the materials of the first electrolyte 201 and the second electrolyte 202. As one example, in a case where a capillary 103 is filled with a sodium carbonate aqueous solution having a concentration of 10 mM, each of the first electrolyte 201 and the second electrolyte 202 is a sodium carbonate aqueous solution having a concentration of 10 mM.

An example of the electrophoretic medium with which the capillary 103 is filled is a buffer solution, an aqueous solution, or pure water. An example of the buffer solution is a boric acid buffer, a phosphate buffer, or a Tris-HCl buffer. The aqueous solution may contain potassium ions, sodium ions, magnesium ions, chloride ions, or carbonate ions. Another example of the aqueous solution is an aqueous solution containing glycine.

The capillary 103 may be filled with the mixture of two or more kinds of electrophoretic mediums. In this case, each of the first electrolyte 201 and the second electrolyte 202 is also composed of the same mixture.

The material of the capillary 103 is not limited, as long as the capillary 103 does not react with the electrophoretic medium and the analytes. An example of the material of the capillary 103 is silica, plastic, silicone, or metal.

(Control Unit 102)

The control unit 102 comprises an alternating-current ammeter in the inside thereof. The details of the control unit 102 will be described later.

(Determining Method)

Hereinafter, a method for determining whether or not the capillary 103 filled with the electrophoretic medium can be used suitably for electrophoresis in the capillary electrophoresis device 100 will be described.

First, the capillary 103 is filled with the electrophoretic medium. Specifically, the electrophoretic medium is supplied to the inside of the first container 106. The electrophoretic medium is also supplied to the inside of the second container 107. Then, the one end 103a of the capillary 103 is immersed in the electrophoretic medium contained in the first container 106. The electrophoretic medium is sucked into the capillary 103 due to a negative pressure. In this way, the inside of the capillary 103 is filled with the electrophoretic medium. A pump may be used. The other end 103b of the capillary 103 is immersed in the electrophoretic medium contained in the second container 107. If necessary, the electrophoretic mediums contained in the first container 106 and in the second container 107 are replaced with other electrolytes. Hereinafter, the present inventors suppose that the first container 106 and the second container 107 contain the first electrolyte 201 and the second electrolyte 202, respectively. Therefore, the one end 103a and the other end 103b are in contact with the first electrolyte 201 and the second electrolyte 202, respectively.

The first electrode 104 and the second electrode 105 are located in the insides of the first container 106 and the second container 107, respectively, in such a manner that the first electrode 104 and the second electrode 105 are in contact with the first electrolyte 201 and the second electrolytes 202, respectively.

Then, an alternating-current voltage is applied between the first electrode 104 and the second electrode 105 using the power supply 101. It is desirable that the applied alternating-current voltage has a voltage of not less than 1 volt and not more than 10 volts. An electric current of a circuit is measured with the alternating-current ammeter comprised in the control unit 102. On the basis of the values of the alternating-current voltage and current, the control unit 102 calculates resistance of the electrophoretic medium with which the capillary 103 has been filled. Furthermore, on the basis of the following mathematical formula (I), the control unit 102 calculates the conductivity of the electrophoretic medium with which the capillary 103 is filled. The unit of the conductivity is S/m, where S represents Siemens and m represents meter.

(Conductivity)=(Electric distance between the first electrode 104 and the second electrode 105)/ ((Cross-sectional area of the capillary 103)·(Resistance value between the first electrode 104 and the second electrode 105))  (I)

Usually, the electric distance between the first electrode 104 and the second electrode 105 is equal to the length of the capillary 103. The accurate electrical distance is represented by the following mathematical formula (II).

(Electrical distance)=(Length of the capillary 103)+ (Shortest distance between the one end 103a and the first electrode 104)+(Shortest distance between the other end 103b and the second electrode 105)  (II)

Then, it is determined whether or not the conductivity is more than 4.2 mS/cm. When the conductivity is over 4.2 mS/cm, it is determined that the capillary 103 fails to be used suitably for electrophoresis. On the other hand, it is determined that the capillary 103 can be used suitably for electrophoresis in a case where the conductivity is not more than 4.2 mS/cm. Desirably, the control unit 102 determines whether or not the conductivity is over 4.2 mS/cm. A user of the capillary electrophoresis device 100 may judge whether or not the conductivity is over 4.2 mS/cm.

As demonstrated in the examples, a baseline of an electropherogram is stable in a case where the conductivity is not more than 4.2 mS/cm. Therefore, using a capillary filled with the electrophoretic medium having the conductivity of not more than 4.2 mS/cm, appropriate electrophoresis is accomplished.

On the other hand, as demonstrated in the comparative examples, the baseline of the electropherogram is unstable in case where the conductivity is beyond 4.2 mS/cm. Therefore, the appropriate electrophoresis fails to be accomplished in case of using a capillary filled with an electrophoretic medium having the conductivity more than 4.2 mS/cm.

In the case where it is determined that the capillary 103 fails to be used for appropriate electrophoresis, the control unit 102 informs the user to that effect. Specifically, the control unit 102 displays that the capillary 103 fails to be used for appropriate electrophoresis on a display device (not shown) connected to the control unit 102. The control unit 102 may inform the user to that effect through a speaker (not shown) connected to the control unit 102.

As just described, in the present embodiment, it is determined whether or not the capillary 103 can be used appropriately for electrophoresis before the analytes are supplied into the capillary 103. In this way, the waste of the analytes is prevented.

Electrophoresis is performed using the capillary 103, after it is determined that the capillary 103 can be used appropriately for electrophoresis. In other words, in a case where it is determined that the capillary 103 can be used appropriately for electrophoresis, the capillary 103 is used for electrophoresis. Specifically, a liquid (desirably, an aqueous solution) containing analytes is supplied to the first container 106. Then, a direct-current voltage is applied between the first electrode 104 and the second electrode 105 to cause the analytes to migrate toward the second container 107 through the inside of the capillary 103. Since each speed of the analytes varies depending on the difference of the electric charges and particle sizes of the analytes, the analytes are separated from one another. An analyte having more electric charge and a smaller particle size reaches the second container 107 through the inside of the capillary 103 quickly, whereas an analyte having less electric charge and larger particle size migrates slowly in the capillary 103. In this way, the analytes are separated from each other due to the electrophoresis using the capillary 103.

The analytes are not limited, as long as the analytes pass through the inside of the capillary 103. An example of the analyte is nucleic acid, protein, a virus, an ionic chemical substance, or a non-ionic chemical substance.

The control unit 102 may be a computer such as a personal computer. Alternatively, the control unit 102 may be one or more of electronic circuits including, but not limited to, a semiconductor device, a semiconductor integrated circuit (IC) or an LSI. The LSI or IC can be integrated into one chip, or also can be a combination of plural chips. For example, functional blocks other than a memory may be integrated into one chip. The name used here is LSI or IC, but it may also be called system LSI, VLSI (i.e., very large scale integration), or ULSI (i.e., ultra large scale integration) depending on the degree of integration. A Field Programmable Gate Array (in short, FPGA) that can be programmed after manufacturing an LSI or a reconfigurable logic device that allows reconfiguration of the connection or setup of circuit cells inside the LSI can be used for the same purpose.

Further, it is also possible that all or a part of the functions or operations of the control unit 102 are implemented by executing software. In such a case, the software is recorded on one or more non-transitory recording media such as a ROM, an optical disk or a hard disk drive, and when the software is executed by a processor such as a computer, the software causes the processor together with peripheral devices to execute the functions specified in the software. A system or apparatus may include such one or more non-transitory recording media on which the software is recorded and a processor together with necessary hardware devices such as an interface.

EXAMPLES

The present invention will be described in more detail with reference to the following examples.

Inventive Example 1

A capillary electrophoresis device 100 (available from Beckman Coulter company, trade name: PA800 plus) shown in FIG. 1 was prepared. The details of a capillary 103 are shown in the following Table 1.

TABLE 1

| | |
|---|---|
| Inner diameter | 50 nanometers |
| Total length | 48.5 centimeters |
| Material | Fused silica |
| Electrophoretic medium | Buffer solution A containing the following materials: 20 mM Tris-HCl (pH 7.5), 5 mM KCl, and 1 mM $MgCl_2$ |

First, the inside of the capillary 103 was washed using a sodium hydroxide aqueous solution having a concentration of 0.1M. In more detail, this sodium hydroxide aqueous solution flowed through the inside of the capillary 103 at a pressure of 138 kPa for two minutes. In this way, the inside of the capillary 103 was washed.

Then, the inside of the capillary 103 was washed using the above-mentioned electrophoretic medium in the same way. A first electrolyte 201 and a second electrolyte 202 were supplied to a first container 106 and a second container 107, respectively. In the inventive example 1, the materials contained in the first electrolyte 201 and the second electrolyte 202 were the same as those of the electrophoretic medium.

An electrophoretic medium was supplied into the thus-washed capillary 103 at a negative pressure of 3.45 kPa for 7.8 seconds. In this way, the inside of the capillary 103 was filled with the electrophoretic medium.

A first electrode 104 and a second electrode 105 were disposed in the insides of the first container 106 and the second container 107, respectively, in such a manner that the first electrode 104 and the second electrode 105 were in contact with the first electrolyte 201 and the second electrolyte 202, respectively.

Then, an alternating-current voltage of 6 volts was applied between the first electrode 104 and the second electrode 105 using a power supply 101. The electric current value of a circuit was measured with an alternating-current ammeter comprised in the control unit 102. The conductivity was calculated on the basis of the mathematical formula (I).

Figure 2A:
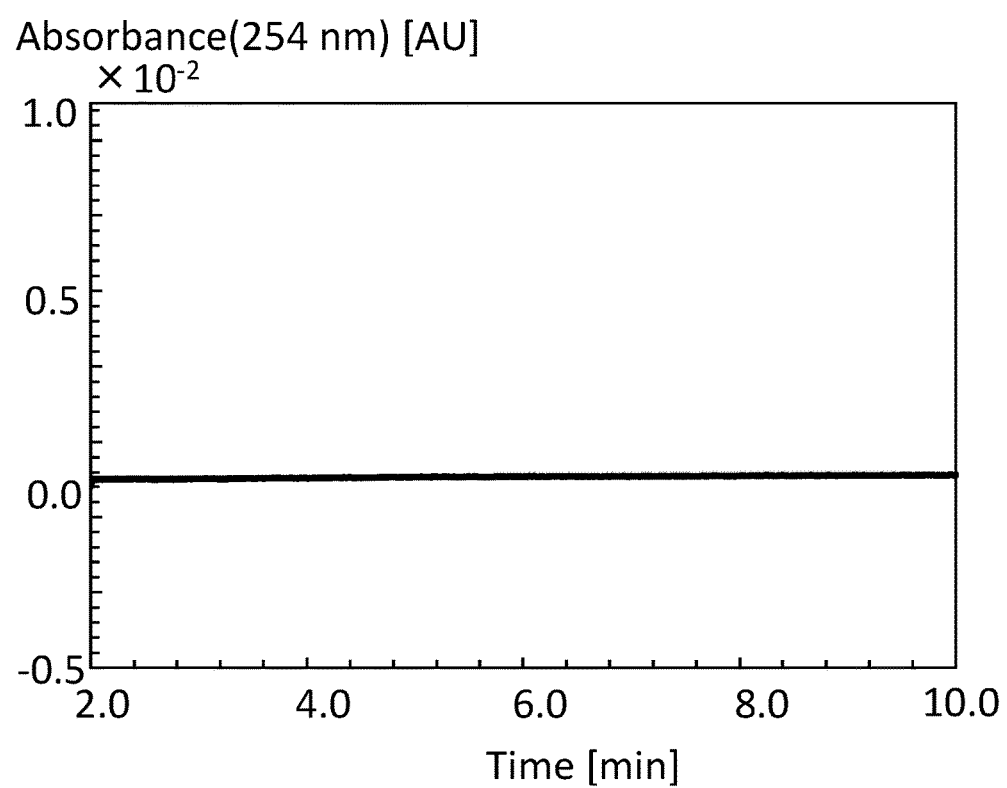
FIG. 2A shows an electropherogram obtained in the inventive example 1.

Furthermore, an electropherogram was obtained, while a direct-current voltage of 30 kV was applied between the first electrode 104 and the second electrode 105 using the power supply 101. FIG. 2A shows an electropherogram obtained in the inventive example 1.

Inventive Examples 2-5 and Comparative Examples 1-7

In the following inventive examples 2-5 and the comparative examples 1-7, the experiments similar to the inventive example 1 were conducted, except for using the electrophoretic mediums identified in the Tables 2-4. The conductivities measured are also shown in the Tables 2-4.

TABLE 2

Figure 2B:
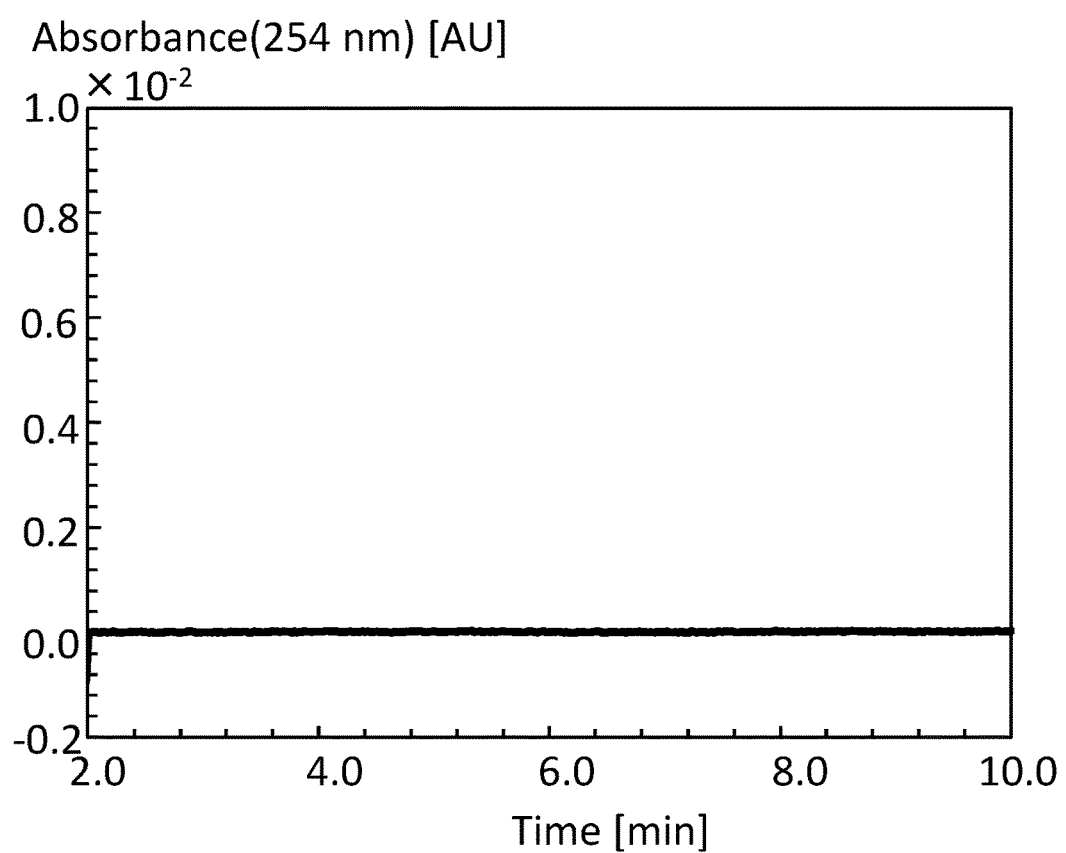
FIG. 2B shows an electropherogram obtained in the inventive example 2.

| | Electrophoretic medium | Conductivity Unit: mS/cm | Electropherogram |
|---|---|---|---|
| Inventive Example 1 | Buffer solution A containing the following materials: 20 mM Tris-HCl (pH 7.5), 5 mM KCl, and 1 mM $MgCl_2$. | 2.20 | FIG. 2A |
| Inventive Example 2 | Buffer solution B containing the following materials: 25 mM Tris-HCl (pH 7.5), 192 mM Glycine, and 5 mM $KH_2PO_4$. | 1.12 | FIG. 2B |

TABLE 2-continued

Figure 2C:
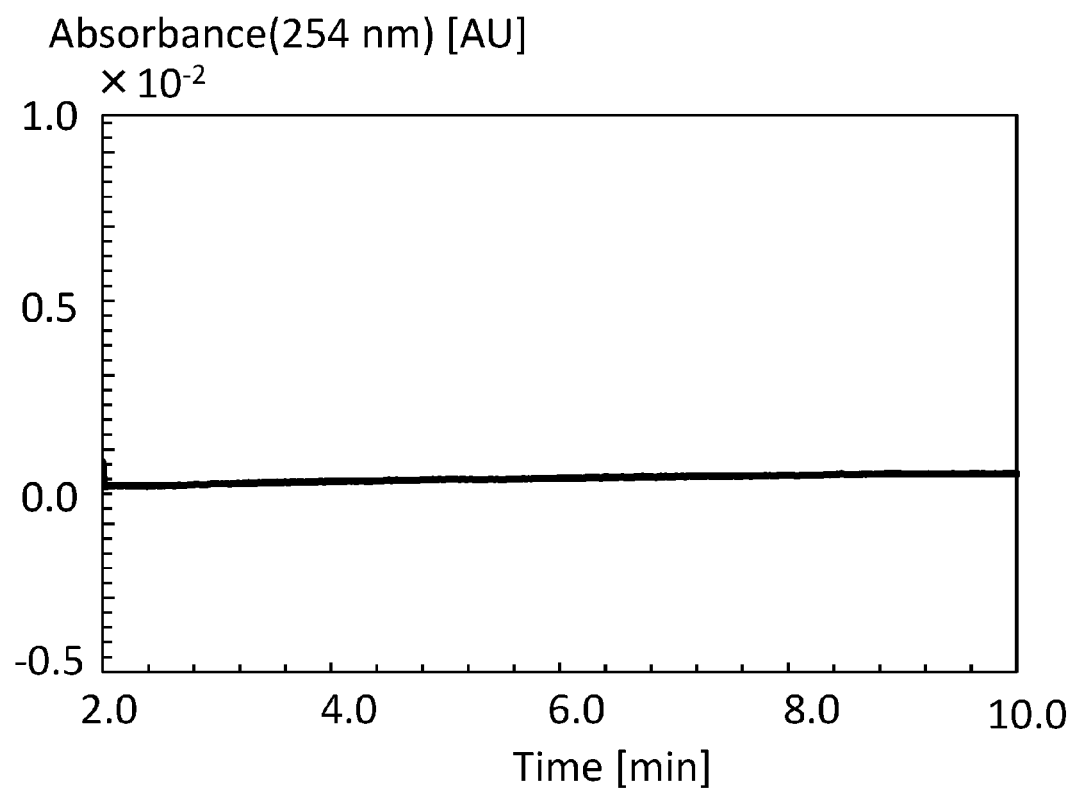
FIG. 2C shows an electropherogram obtained in the inventive example 3.
Figure 2D:
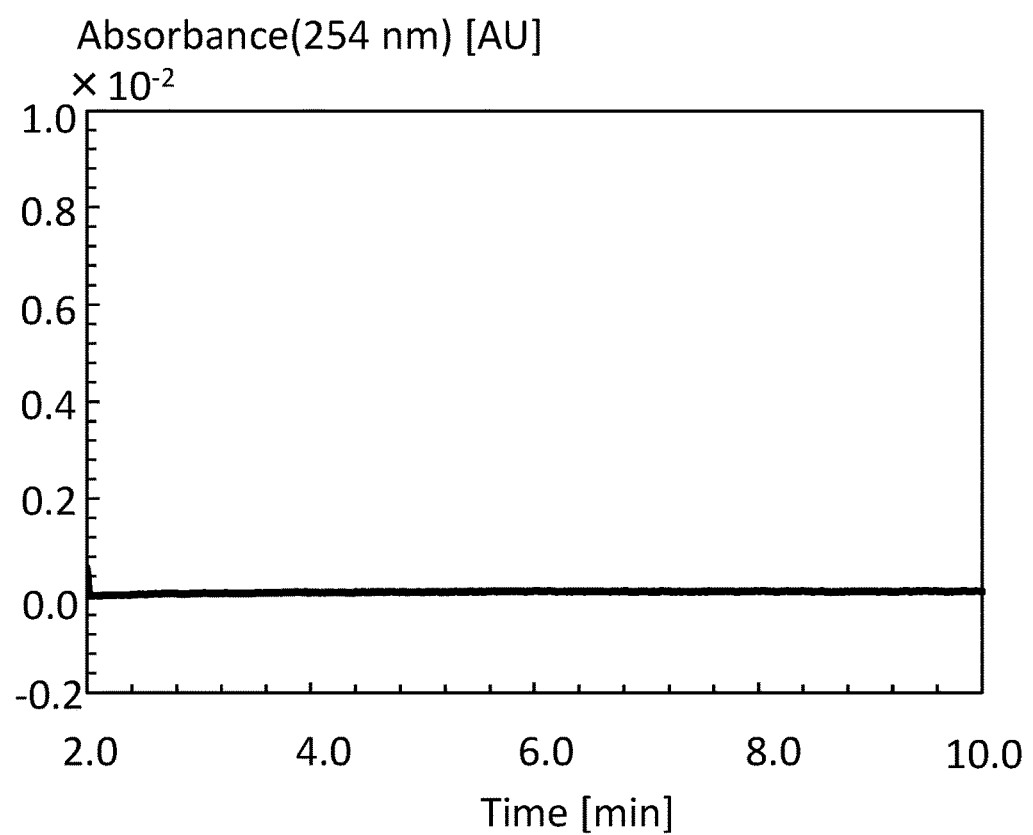
FIG. 2D shows an electropherogram obtained in the inventive example 4.
Figure 2E:
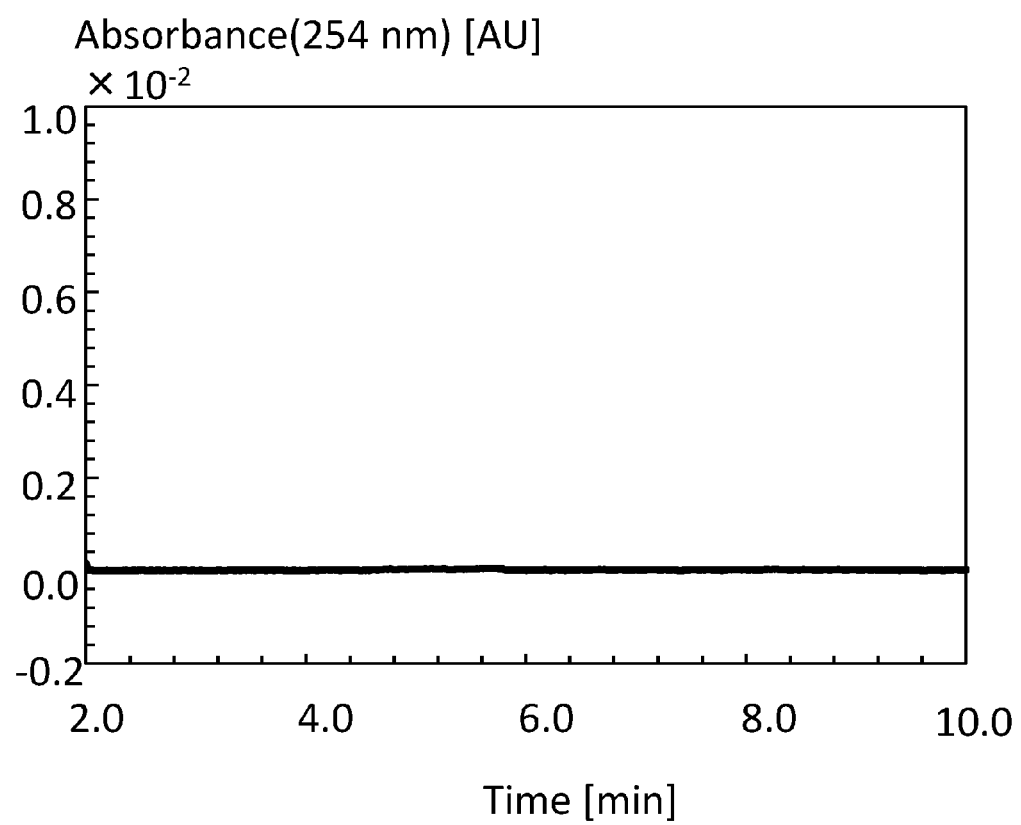
FIG. 2E shows an electropherogram obtained in the inventive example 5.

| | Electrophoretic medium | Conductivity Unit: mS/cm | Electropherogram |
|---|---|---|---|
| Inventive Example 3 | Buffer solution C containing the following material: 100 mM $Na_2P_4O_7 \cdot 10H_2O$. | 1.40 | FIG. 2C |
| Inventive Example 4 | Buffer solution D containing the following material: 10 mM $Na_4P_2O_7 \cdot 10H_2O$. | 3.00 | FIG. 2D |
| Inventive Example 5 | Buffer solution E containing the following material: 10 mM $Na_2CO_3$. | 2.20 | FIG. 2E |

TABLE 3

Figure 2F:
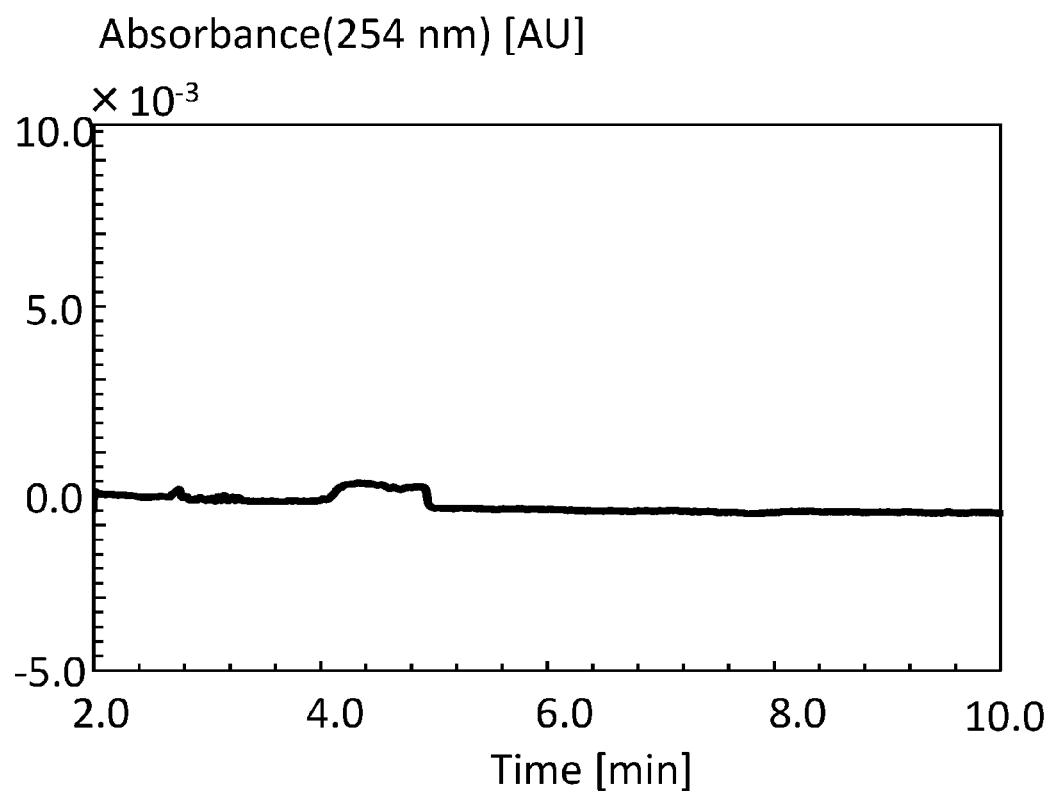
FIG. 2F shows an electropherogram obtained in the comparative example 1.
Figure 2G:
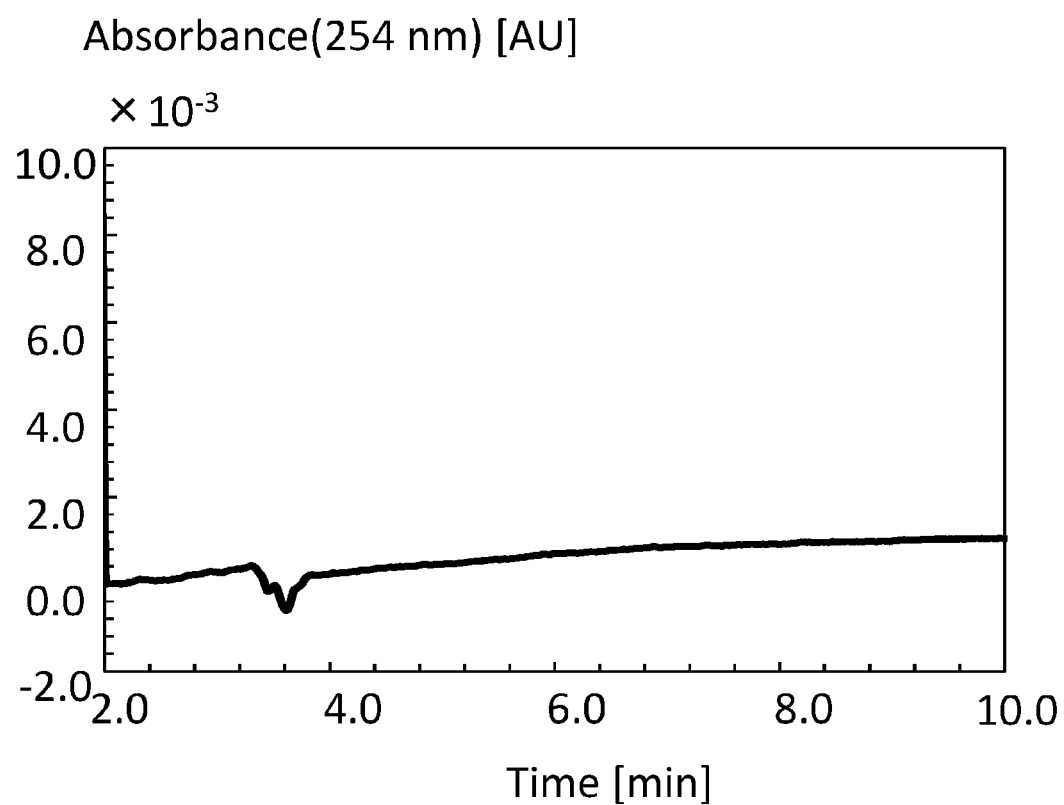
FIG. 2G shows an electropherogram obtained in the comparative example 2.
Figure 2H:
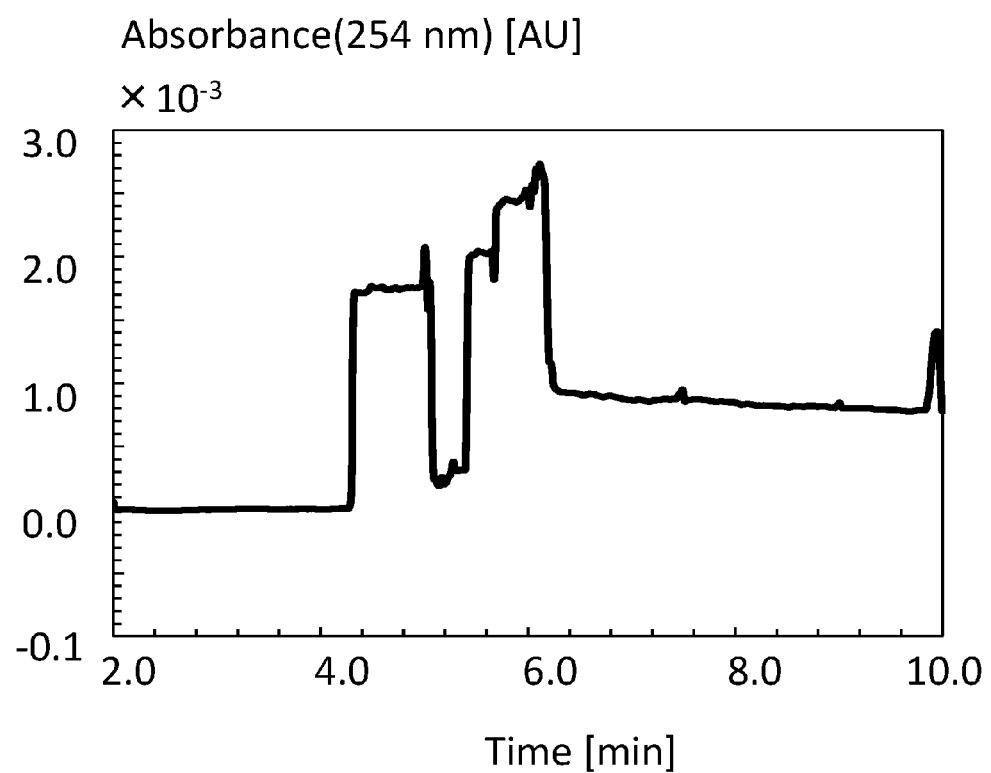
FIG. 2H shows an electropherogram obtained in the comparative example 3.
Figure 2I:
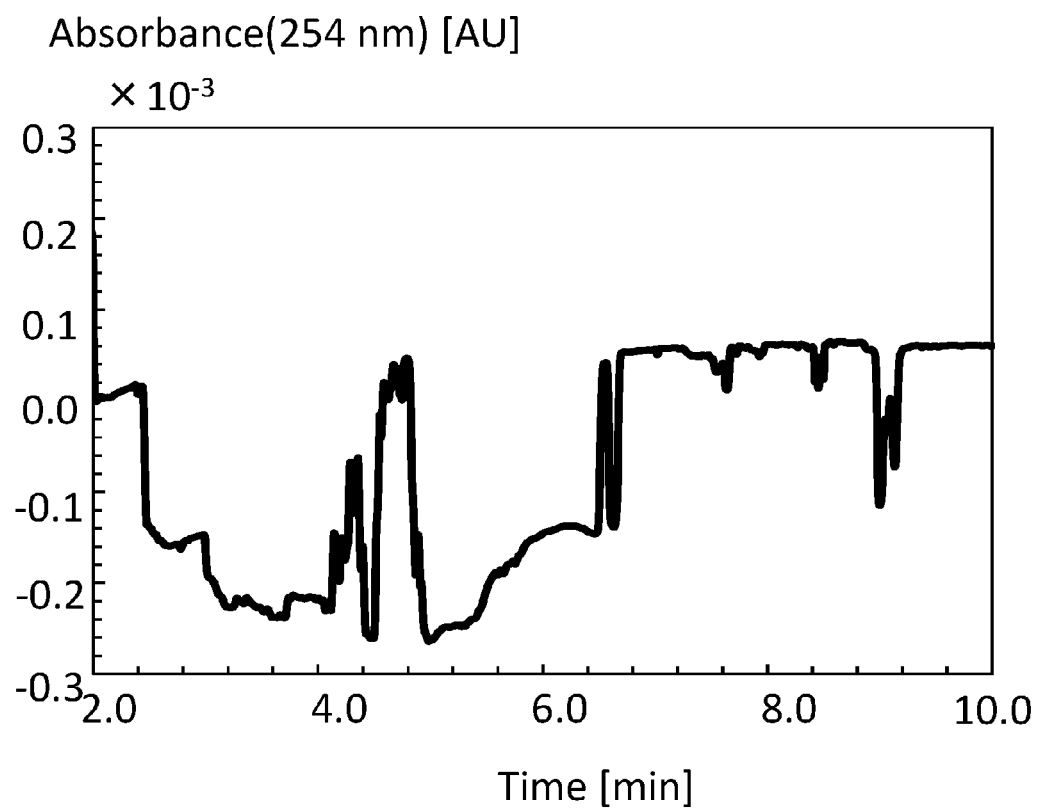
FIG. 2I shows an electropherogram obtained in the comparative example 4.
Figure 2J:
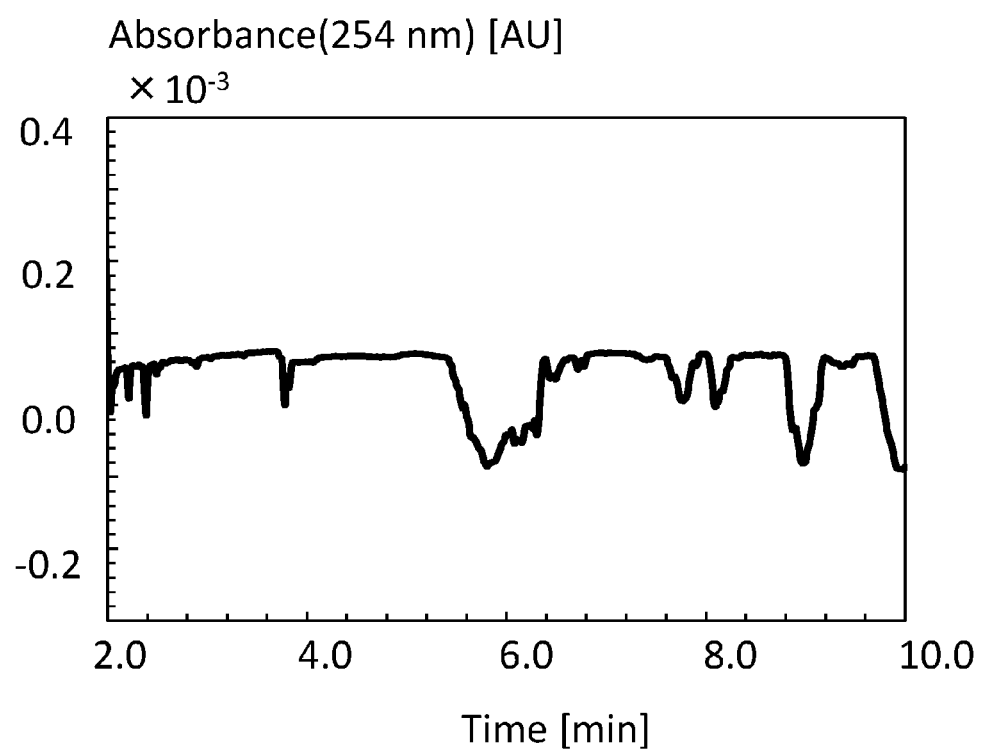
FIG. 2J shows an electropherogram obtained in the comparative example 5.

| | Electrophoretic medium | Conductivity Unit: mS/cm | Electropherogram |
|---|---|---|---|
| Comparative example 1 | Buffer solution F containing the following materials: 20 mM Tris-HCl (pH 7.4), 140 mM NaCl, 5 mM KCl, and 5 mM $MgCl_2$. | 19.4 | FIG. 2F |
| Comparative example 2 | Buffer solution B containing the following materials: 20 mM Tris-HCl (pH 7.5), 140 mM NaCl, 5 mM KCl and 1 mM $MgCl_2$. | 15.2 | FIG. 2G |
| Comparative example 3 | Buffer solution C containing the following materials: 140 mM NaCl, 5 mM KCl, and 1 mM $MgCl_2$. | 13.7 | FIG. 2H |
| Comparative example 4 | Buffer solution D containing the following materials: 20 mM Tris-HCl (pH 7.5), 140 mM NaCl, and 1 mM $MgCl_2$. | 14.2 | FIG. 2I |
| Comparative example 5 | Buffer solution E containing the following materials: 20 mM Tris-HCl (pH 7.5), 140 mM NaCl, and 5 mM KCl. | 14.6 | FIG. 2J |

TABLE 4

Figure 2K:
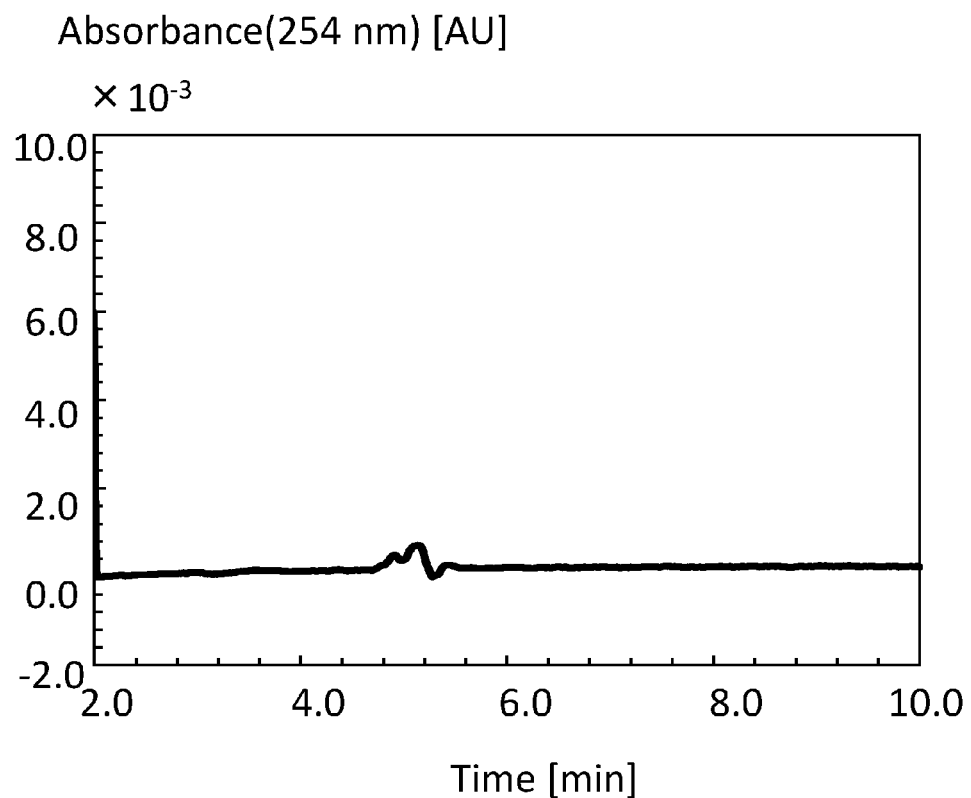
FIG. 2K shows an electropherogram obtained in the comparative example 6.
Figure 2L:
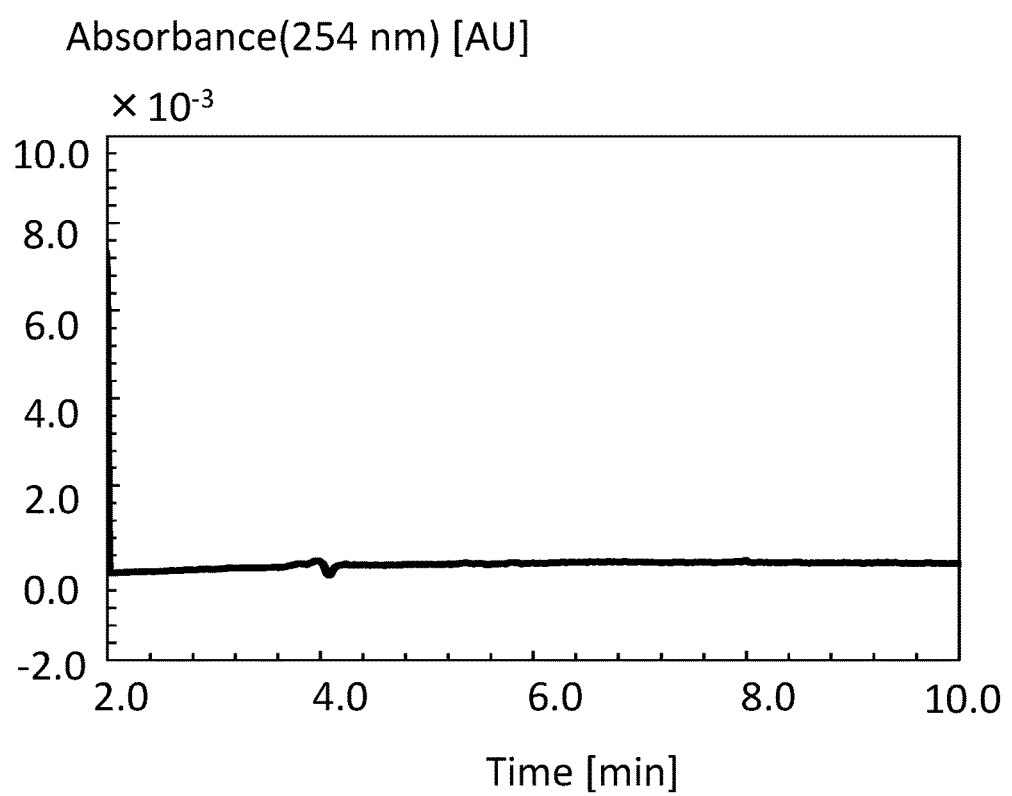
FIG. 2L shows an electropherogram obtained in the comparative example 7.

| | Electrophoretic medium | Conductivity Unit: mS/cm | Electropherogram |
|---|---|---|---|
| Comparative example 6 | Buffer solution F containing the following material: 100 mM $Na_4P_2O_7 \cdot 10H_2O$. | 16.4 | FIG. 2K |
| Comparative example 7 | Buffer solution G containing the following material: 100 mM $Na_2CO_3$. | 13.2 | FIG. 2L |

As is clear from Table 2 and FIG. 2A-FIG. 2E, the baseline of the electropherogram is stable in a case where the conductivity is not more than 4.2 mS/cm. In other words, the base line is substantially flat. For this reason, the appropriate electrophoresis is conducted using such a capillary 103.

On the other hand, as is clear from Table 3-Table 4 and FIG. 2F-FIG. 2L, the baseline of the electropherogram is unstable in case where the conductivity is more than 4.2 mS/cm. In other words, the baseline is not flat and has protrusions and recesses. For this reason, the appropriate electrophoresis fails to be conducted if such a capillary 103 is used.

INDUSTRIAL APPLICABILITY

The method according to the present invention is conducted prior to the electrophoresis for the separation of nucleic acid, protein, a virus, an ionic chemical substance, or a non-ionic chemical substance in order to determine whether or not an electrophoresis is appropriately conducted using a capillary filled with an electrophoresis medium.

REFERENTIAL SIGNS LIST

100 Capillary electrophoresis device
101 Power supply
102 Control unit
103 Capillary
103a One end
103b The other end
104 First electrode
105 Second electrode
106 First container
107 Second container
108 Sample
201 First electrolyte
202 Second electrolyte

The invention claimed is:

1. A method for determining whether or not a capillary filled with an electrophoresis medium can be used suitably for electrophoresis, the method comprising;
    (a) applying an alternating-current voltage between a first electrode which is in contact with a first electrolyte solution in which one end of the capillary is immersed and a second electrode which is in contact with a second electrolyte solution in which the other end of the capillary is immersed to measure an electric conductivity of the electrophoresis medium with which an inside of the capillary is filled; and
    (b) determining that the capillary filled with the electrophoresis medium fails to be used suitably for the electrophoresis, when the electric conductivity is more than 4.2 mS/cm.

2. The method according to claim 1, wherein
the first electrode and the second electrode have a shape of a flat plate.

3. The method according to claim 1, wherein
the electrophoresis medium, the first electrolyte solution, and the second electrolyte solution have a same composition.

4. An electrophoresis method, comprising:
    (a) applying an alternating-current voltage between a first electrode which is in contact with a first electrolyte solution in which one end of a capillary is immersed and a second electrode which is in contact with a second electrolyte solution in which the other end of the capillary is immersed to measure an electric conductivity of an electrophoresis medium with which an inside of the capillary is filled; and
    (b) applying a direct current between the first electrode and the second electrode to perform electrophoresis through the capillary between the first electrolyte solution and the second electrolyte solution, if the electric conductivity is not more than 4.2 mS/cm.

5. The method according to claim 4, wherein
the first electrode and the second electrode have a shape of a flat plate.

6. The method according to claim 4, wherein the electrophoresis medium, the first electrolyte solution, and the second electrolyte solution have a same composition.

\* \* \* \* \*